US006628989B1

(12) United States Patent
Penner et al.

(10) Patent No.: US 6,628,989 B1
(45) Date of Patent: Sep. 30, 2003

(54) ACOUSTIC SWITCH AND APPARATUS AND METHODS FOR USING ACOUSTIC SWITCHES WITHIN A BODY

(75) Inventors: Avi Penner, Tel Aviv (IL); Eyal Doron, Kiryat Yam (IL)

(73) Assignee: Remon Medical Technologies, Ltd., Caesarea (IL)

( * ) Notice: Subject to any disclaimer, the term of this patent is extended or adjusted under 35 U.S.C. 154(b) by 152 days.

(21) Appl. No.: 09/690,615

(22) Filed: Oct. 16, 2000

(51) Int. Cl.⁷ .......................... A61N 1/372; A61B 5/00
(52) U.S. Cl. .............. 607/59; 607/60; 607/30; 604/891.1; 600/377; 310/322
(58) Field of Search .............. 607/59, 60, 61, 607/62, 66, 116, 119, 30–35; 604/891.1; 600/373, 377; 310/322, 334, 335

(56) References Cited

U.S. PATENT DOCUMENTS

| | | | |
|---|---|---|---|
| 2,786,899 A | | 3/1957 | Carlisle |
| 3,672,352 A | | 6/1972 | Summers |
| 3,970,987 A | | 7/1976 | Kolm |
| 4,041,954 A | | 8/1977 | Ohara |
| 4,099,530 A | | 7/1978 | Chen et al. |
| 4,481,950 A | * | 11/1984 | Duggan .................. 607/29 |
| 4,616,640 A | * | 10/1986 | Kaali et al. .............. 607/138 |
| 4,651,740 A | | 3/1987 | Schroeppel |
| 4,793,825 A | | 12/1988 | Benjamin et al. |
| 5,113,859 A | | 5/1992 | Funke |
| 5,833,603 A | | 11/1998 | Kovacs et al. |
| 6,140,740 A | | 10/2000 | Porat et al. |
| 6,162,238 A | * | 12/2000 | Kaplan et al. ........... 606/201 |
| 6,170,488 B1 | * | 1/2001 | Spillman, Jr. et al. .... 128/899 |
| 6,200,265 B1 | | 3/2001 | Walsh et al. |
| 6,236,889 B1 | | 5/2001 | Soykan et al. |

FOREIGN PATENT DOCUMENTS

| | | |
|---|---|---|
| WO | WO 99/34453 | 7/1999 |
| WO | WO 01/28627 A1 | 4/2001 |
| WO | WO 01/74278 A2 | 10/2001 |
| WO | WO 01/74278 A3 | 10/2001 |

OTHER PUBLICATIONS

Y. Porat,, et al., "Method for Transfer of Energy to an Electronic Circuit Implanted in a Living Body and a Device for Such Method", PCT Publication No. WO 98/43338, Oct. 1, 1998.
M. M. Friedman, "Piezoelectric Transducer", PCT Publication No. WO 99/34453, Jul. 8, 1999.
PCT Publication No. WO 00/47109 entitled Devices and Methods for Frequent Measurement of an Analyte Present in a Biological System. Aug, 17, 2000.

* cited by examiner

Primary Examiner—Philip H. Leung
(74) Attorney, Agent, or Firm—Bingham McCutchen LLP (57) ABSTRACT

An implant for insertion or implantation within a body includes an electrical circuit for performing one or more commands when the implant is activated, an energy storage device, and a switch coupled to the electrical circuit and the energy storage device. An acoustic transducer is coupled to the switch, the acoustic transducer being activatable upon acoustic excitation by an external acoustic energy source for closing the switch to allow current flow from the energy storage device to the electrical circuit. The one or more commands includes measuring a physiological parameter with a biosensor coupled to the electrical circuit, or controlling a therapeutic device coupled to the electrical circuit. The therapeutic device or biosensor may be activated for a predetermined time or until the switch is opened in response to another acoustic excitation of the acoustic transducer.

26 Claims, 8 Drawing Sheets

ACOUSTIC SWITCH AND APPARATUS AND METHODS FOR USING ACOUSTIC SWITCHES WITHIN A BODY

INTRODUCTION

The present invention relates generally to devices for implantation within a patient's body, and more particularly to devices for activating, deactivating, and/or controlling implants located within a body that monitor physiological conditions and/or provide therapeutic functions.

BACKGROUND OF THE INVENTION

Devices are known that may be implanted within a patient's body to monitor one or more physiological conditions and/or to provide therapeutic functions. For example, sensors or transducers may be located deep within the body for monitoring a variety of properties, such as temperature, pressure, strain, fluid flow, chemical properties, electrical properties, magnetic properties, and the like. In addition, devices may be implanted that perform one or more therapeutic functions, such as drug delivery, defibrillation, electrical stimulation, and the like.

Often it is desirable to control by external command such devices once they are implanted within a patient, for example, to obtain data, and/or to activate or otherwise control the implant. An implant may include wire leads from the implant to an exterior surface of the patient, thereby allowing an external controller or other device to be directly coupled to the implant. Alternatively, the implant may be remotely controlled, for example, using an external induction device. For example, an external radio frequency (RF) transmitter may be used to communicate with the implant. RF energy, however, may only penetrate a few millimeters into a body, because of the body's dielectric nature, and therefore may not be able to communicate effectively with an implant that is located deep within the body. In addition, although an RF transmitter may be able to induce a current within an implant, the implant's receiving antenna, generally a low impedance coil, may generate a voltage that is too low to provide a reliable switching mechanism.

In a further alternative, electromagnetic energy may be used to switch or otherwise control an implant, since a body generally does not attenuate magnetic fields. The presence of external magnetic fields encountered by the patient during normal activity, however, may expose the patient to the risk of false positives, i.e., accidental activation or deactivation of the implant. Furthermore, external electromagnetic systems may be cumbersome and may not be able to effectively transfer coded information to an implant.

Accordingly, it is believed that a device that overcomes these problems and/or that may more effectively remotely activate or otherwise control an implant located within a patient's body may be considered useful.

SUMMARY OF THE INVENTION

The present invention is generally directed to implants that may be surgically or otherwise located within a mammalian body for monitoring one or more physiological parameters and/or for performing one or more therapeutic functions. For example, an implant in accordance with the present invention may be used for atrial defibrillation, pain relief stimulation, neuro-stimulation, drug release, activation of a light source for photodynamic therapy, monitoring of a radiation dose including ionizing, magnetic or acoustic radiation, monitoring of flow in a bypass graft, producing cell oxygenation and membrane electroportation, and measurement of various physiological parameters including heart chamber pressure, infraction temperature, intracranial pressure, electrical impedance, position, orthopedic implant strain or pH.

In a accordance with a first aspect of the present invention, an implant is provided that includes an electrical circuit configured for performing one or more commands when the implant is activated, an energy storage device, and a switch coupled to the electrical circuit and the energy storage device. An acoustic transducer is coupled to the switch that may be activated upon acoustic excitation by an external acoustic energy source for closing the switch to allow current flow from the energy storage device to the electrical circuit.

In one embodiment, the switch may be closed only when the acoustic transducer receives a first acoustic initiation signal followed by a second acoustic confirmation signal, the first and second acoustic signals being separated by a predetermined delay.

The switch may remain closed for a predetermined time and then automatically open. Alternatively or in addition, the switch may be opened when an acoustic termination signal is received by the acoustic transducer for discontinuing current flow from the energy storage device to the electrical circuit.

In one preferred embodiment, the electrical circuit includes a sensor for measuring a physiological parameter within the body. A transmitter or the acoustic transducer itself may be coupled to the electrical circuit for receiving an electrical signal proportional to the physiological parameter measured by the sensor. The transmitter or acoustic transducer may transmit a signal including information regarding the physiological parameter to a receiver located outside the body. Preferably, the sensor is a biosensor configured for measuring at least one of blood pressure, heart chamber pressure, infraction temperature, intracranial pressure, electrical impedance, position, orthopedic implant strain, or pH, and the acoustic transducer enables communication of data from the sensor to a receiver located outside the body.

In another preferred embodiment, the electrical circuit includes an actuator for activating or controlling a therapeutic device within the body that is connected to or otherwise associated with the actuator. The electrical circuit may activate the therapeutic device for a predetermined time, or until the switch is opened. Alternatively, the electrical circuit may control the therapeutic device in response to a physiological parameter measured by a biosensor coupled to the electrical circuit.

During use, the acoustic transducer may receive a relatively low frequency acoustic signal that vibrates the piezoelectric layer at its resonant frequency. The acoustic signal closes the switch, activating the implant from its "sleep" mode to an "active" mode. In the sleep mode, the implant may wait substantially indefinitely with substantially no energy consumption. Once activated, i.e., when the switch is closed, the electrical circuit performs one or more commands, such as measuring a physiological parameter within the body, or controlling a therapeutic device within the body. A signal proportional to the physiological parameter may be transmitted from the implant to a receiver located outside the body. Alternatively, the therapeutic device may be controlled based upon the physiological parameter.

In a further alternative, a set of command signals may be sent from a source outside the body along with or after the acoustic activation signal. The command signals may be interpreted by the electrical circuit to provide a set of commands to control the therapeutic device, e.g., to provide a desired course of treatment. For example, the commands may instruct the therapeutic device to provide a desired dosage for a desired duration, and/or may modify dosage or duration based upon feedback from the biosensor.

Other objects and features of the present invention will become apparent from consideration of the following description taken in conjunction with the accompanying drawings.

BRIEF DESCRIPTION OF THE DRAWINGS

The invention is herein described, by way of example only, with reference to the accompanying drawings, wherein.

DESCRIPTION OF THE PREFFERED EMBODIMENT

Figure 1A:
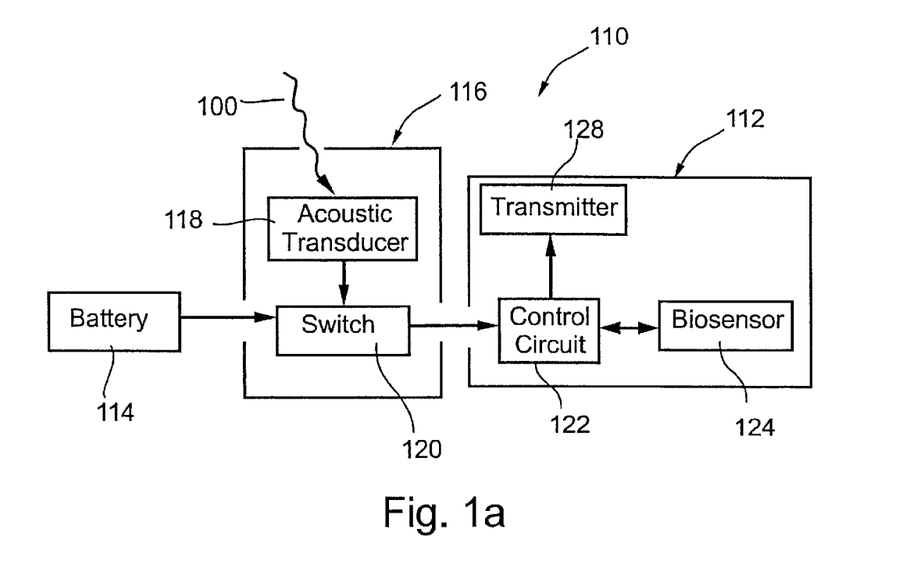
FIGS. 1A–1C are block diagrams, showing exemplary embodiments of an implant, in accordance with the present invention.
Figure 1B:
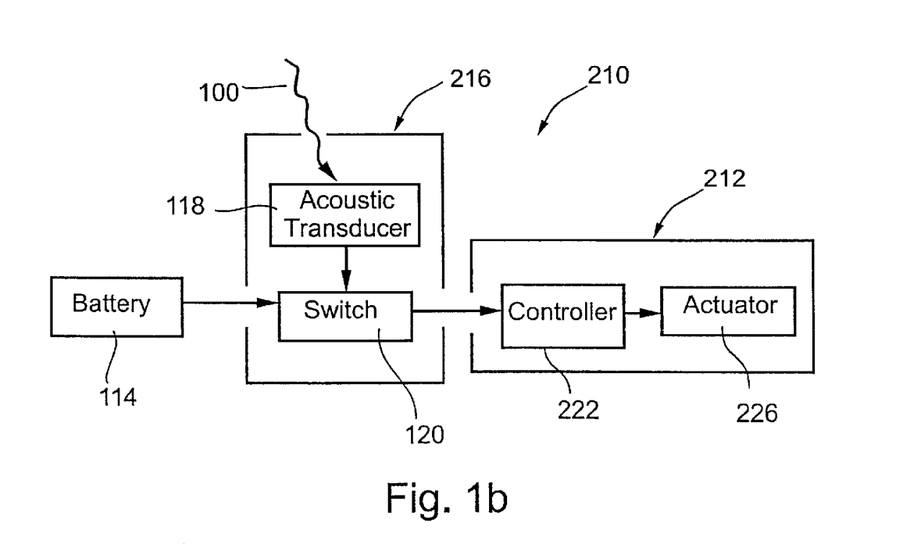
Figure 1C:
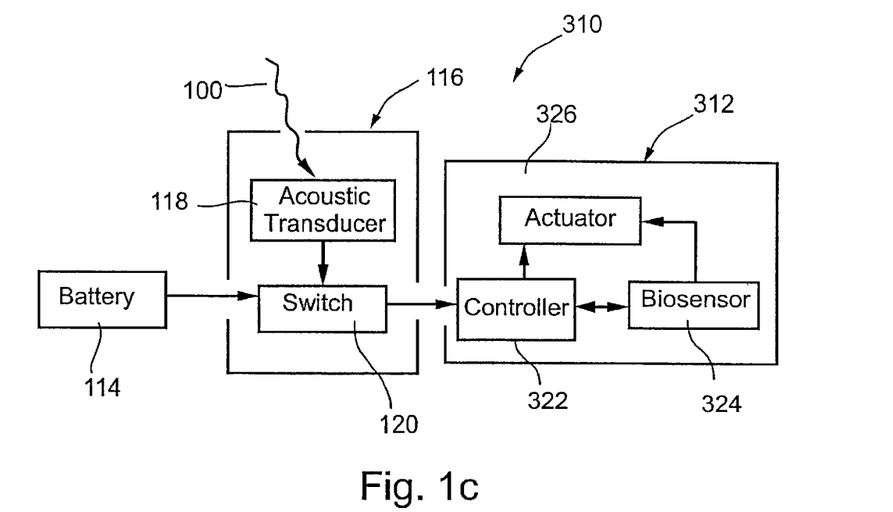

Turning to the drawings, FIGS. 1A–1C schematically show several exemplary embodiments of an implant 110, 210, 310, in accordance with the present invention. Generally, the implant 110, 210, 310 includes an electrical circuit 112, 212, 312 configured for performing one or more functions or commands when the implant 110, 210, 310 is activated, as described further below. In addition, the implant 110, 210, 310 includes an energy storage device 114 and an acoustic switch 116 coupled to the electrical circuit 112, 212, 312 and the energy storage device 114. The acoustic switch 116 is preferably activated upon acoustic excitation 100 by an external acoustic energy source (not shown) to allow current flow from the energy storage device 114 to the electrical circuit 112, 212, 312. In a preferred embodiment, the acoustic switch 116 includes an acoustic transducer 118, such as that disclosed in PCT Publication No. WO 99/34,453, published Jul. 8, 1999, the disclosure of which is expressly incorporated herein by reference. In addition, the acoustic switch 116 also includes a switch 120, such as switch circuit 400 shown in FIG. 2 and described further below, although alternatively other switches, such as a miniature electromechanical switch and the like (not shown) may be provided.

The energy storage device 114 may be any of a variety of known devices, such as an energy exchanger, a battery and/or a capacitor (not shown). Preferably, the energy storage device 114 is capable of storing electrical energy substantially indefinitely for as long as the acoustic switch 116 remains open, i.e., when the implant 110, 210, 310 is in a "sleep" mode. In addition, the energy storage device 114 may be capable of being charged from an external source, e.g., inductively, as will be appreciated by those skilled in the art. In a preferred embodiment, the energy storage device 114 includes both a capacitor and a primary, non-rechargeable battery. Alternatively, the energy storage device 114 may include a secondary, rechargeable battery and/or capacitor that may be energized before activation or use of the implant 110, 210, 310.

The implant 110, 210, 310 may be surgically or minimally invasively inserted within a human body in order to carry out a variety of monitoring and/or therapeutic functions. For example, the electrical circuit 112, 212, 312 may include a control circuit 122, 222, 322, a biosensor 124, 224, an actuator 226, 326, and/or a transmitter 128, as explained in more detail below. The implant 210, 310 may be configured for providing one or more therapeutic functions, for example, to activate and/or control a therapeutic device implanted within a patient's body, such as an atrial defibrillator, a pain relief stimulator, a neuro-stimulator, a drug delivery device, and/or a light source used for photo-dynamic therapy. Alternatively, the implant may be used to monitor a radiation dose including ionizing, magnetic and/or acoustic radiation, to monitor flow in a bypass graft, to produce cell oxygenation and membrane electroportation, and the like. In addition or alternatively, the implant 110 may be used to measure one or more physiological parameters within the patient's body, such as pressure, temperature, electrical impedance, position, strain, pH, and the like.

An implant in accordance with the present invention operates in one of two modes, a "sleep" or "passive" mode when the implant remains dormant and not in use, i.e., when the acoustic switch 116 is open, and an "active" mode, when the acoustic switch 116 is closed, and electrical energy is delivered from the energy storage device 114 to the electrical circuit 112, 212, 312. Because the acoustic switch 116 is open in the sleep mode, there is substantially no energy consumption from the energy storage device 114, and consequently, the implant may remain in the sleep mode virtually indefinitely, i.e., until activated. Thus, an implant in accordance with the present invention may be more energy efficient and, therefore, may require a relatively small energy storage device than implants that continuously draw at least a small amount of current in their "passive" mode.

To activate the implant 110, 210, 310, one or more external acoustic energy waves or signals 100 are transmitted from an external source into the patient's body (not shown), e.g., generally towards the location of the implant 110, 210, 310 until the signal is received by the acoustic transducer 118. Upon excitation by the acoustic wave(s) 100, the acoustic transducer 118 produces an electrical output that is used to close, open, or otherwise activate the switch 120. Preferably, in order to achieve reliable switching, the acoustic transducer 118 is configured to generate a voltage of at least several tenths of a volt upon excitation that may be used as an activation signal to close the switch 120.

As a safety measure against false positives (either erroneous activations or deactivations), the acoustic switch 116 may be configured to close only upon receipt of an initiation signal followed by a confirmation signal. For example, the acoustic switch 116 may only acknowledge an activation signal that includes a first pulse followed by a second pulse separated by a predetermined delay. Use of a confirmation signal may be particularly important for certain applications, for example, to prevent unintentional release of drugs by a drug delivery implant.

In addition to an activation signal, the acoustic transducer 118 may be configured for generating a termination signal in response to a second acoustic excitation (which may be the same or different than the acoustic wave(s) used to activate the acoustic switch 116) in order to return the implant 110, 210, 310 to its sleep mode. For example, once activated, the switch 120 may remain closed indefinitely, e.g., until the energy storage device 114 is depleted or until a termination signal is received by the acoustic transducer 118. Alternatively, the acoustic switch 116 may include a timer (not shown), such that the switch 120 remains closed only for a predetermined time, whereupon the switch 120 may automatically open, returning the implant 110, 210, 310 to its sleep mode.

Turning to FIG. 1A, a first preferred embodiment of an implant 110 is shown in which the electrical circuit 112 includes a controller 122, a biosensor 124 coupled to the controller 122, and a transmitter 128 coupled to the controller 122. The controller 122 may include circuitry for activating or controlling the biosensor 124, for receiving signals from the biosensor 124, and/or for processing the signals into data, for example, to be transmitted by the transmitter 128. Optionally, the electrical circuit 112 may include memory (not shown) for storing the data. The transmitter 128 may be any device capable of transmitting data from the controller 122 to a remote location outside the body, such as an acoustic transmitter, a radio frequency transmitter, and the like. In an alternative embodiment, the controller 122 may be coupled to the acoustic transducer 118 such that the acoustic transducer 118 may be used as a transmitter 128 instead of providing a separate transmitter.

The biosensor 124 may include one or more sensors capable of measuring physiological parameters, such as those described above. For example, U.S. Pat. No. 4,793,825 issued in the name of Benjamin et al. and U.S. Pat. No. 5,833,603 issued in the name of Kovacs et al. disclose exemplary embodiments of biosensors that may be included in an implant, in accordance with the present invention. The disclosure of these references and others cited therein are expressly incorporated herein by reference. Thus, the biosensor 124 may generate a signal proportional to a physiological parameter that may be processed and/or relayed by the controller 122 to the transmitter 128, which may, in turn, generate a transmission signal to be received by a device outside the patient's body. Data regarding the physiological parameter(s) may be transmitted continuously or periodically until the acoustic switch 116 is deactivated, or for a fixed predetermined time, as will be appreciated by those skilled in the art.

Turning to FIG. 1B, a second preferred embodiment of an implant 210 is shown in which the electrical circuit 212 includes a controller 222 and an actuator 226. The actuator 226 may be coupled to a therapeutic device (not shown) provided in or otherwise coupled to the implant 210, such as a light source, a nerve stimulator, a defibrillator, or a valve communicating with an implanted drug reservoir (in the implant or otherwise implanted within the body in association with the implant). For example, the actuator 226 may be a light source for photo-dynamic therapy, such as that disclosed in U.S. Pat. No. 5,800,478 issued in the name of Chen et al., the disclosure of which is expressly incorporated herein by reference.

When the switch 120 is closed, the controller 222 may activate the actuator 226 using a pre-programmed protocol, e.g., to complete a predetermined therapeutic procedure, whereupon the switch 120 may automatically open, or the controller 222 may follow a continuous or looped protocol until the switch 120 is deactivated. Alternatively, the acoustic transducer 118 may be coupled to the controller 222 for communicating a new or unique set of commands to the controller 222. For example, a particular course of treatment for a patient having the implant 210 may be determined, such as a flow rate and duration of drug delivery or an energy level and duration of electrical stimulation. Acoustic signals including commands specifying this course of treatment may be transmitted from an external device (not shown) to the acoustic switch 116, e.g., along with or subsequent to the activation signal 100. The controller 222 may interpret these commands and control the actuator 226 accordingly to complete the course of treatment.

Turning to FIG. 1C, yet another preferred embodiment of an implant 310 is shown in which the electrical circuit 312 includes a controller 322, a biosensor 324, and an actuator 326, all of which may be coupled to one another. This embodiment may operate similarly to the embodiments described above, e.g., to obtain data regarding one or more physiological parameters and/or to control a therapeutic device. In addition, once activated, the controller 322 may control the actuator 326 in response to data obtained from the biosensor 324 to automatically control or adjust a course of treatment being provided by a device connected to the actuator 326. For example, the actuator 326 may be coupled to an insulin pump (not shown), and the biosensor 324 may measure glucose levels within the patient's body. The controller 322 may control the actuator to open or close a valve on the insulin pump to adjust a rate of insulin delivery based upon glucose levels measured by the biosensor 324 in order to maintain the patient's glucose within a desired range.

Figure 2:
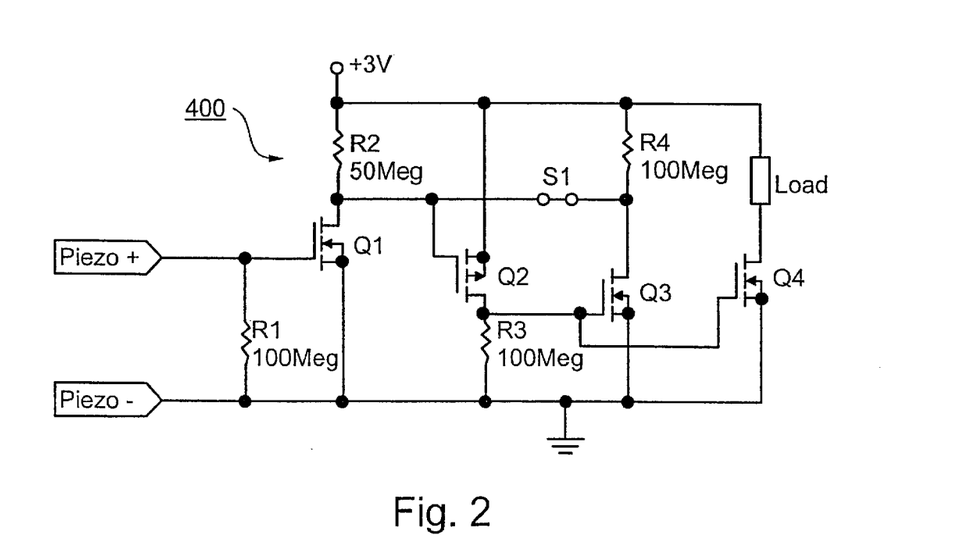
FIG. 2 is a schematic diagram, showing a preferred embodiment of an electrical switch circuit, in accordance with the present invention.

Turning to FIG. 2, a preferred embodiment of a switch 400 is shown that may be incorporated into an implant in accordance with the present invention. The switch 400 includes a piezoelectric transducer, or other acoustic transducer (not shown, but generally connected to the switch 400 at locations piezo+ and piezo−), a plurality of MOSFET transistors (Q1–Q4) and resistors (R1–R4), and switch S1. A "load" may be coupled to the switch 400, such as one of the electrical circuits described above. In the switch's "sleep" mode, all of the MOSFET transistors (Q1–Q4) are in an off state. To maintain the off state, the gates of the transistors are biased by pull-up and pull-down resistors. The gates of N-channel transistors (Q1, Q3 & Q4) are biased to ground and the gate of P-channel transistor Q2 is biased to +3V. During this quiescent stage, switch S1 is closed and no current flows through the circuit. Therefore, although an energy storage device (not shown, but coupled between the hot post, labeled with an exemplary voltage of +3V, and ground) is connected to the switch 400, no current is being drawn therefrom since all of the transistors are quiescent.

When the piezoelectric transducer detects an external acoustic signal, e.g., having a particular frequency such as the transducer's resonant frequency, the voltage on the transistor Q1 will exceed the transistor threshold voltage of about one half of a volt. Transistor Q1 is thereby switched on and current flows through transistor Q1 and pull-up resistor R2. As a result of the current flow through transistor Q1, the voltage on the drain of transistor Q1 and the gate of transistor Q2 drops from +3V substantially to zero (ground). This drop in voltage switches on the P-channel transistor Q2, which begins to conduct through transistor Q2 and pull-down resistor R3.

As a result of the current flowing through transistor Q2, the voltage on the drain of transistor Q2 and the gates of transistors Q3 and Q4 increases from substantially zero to +3V. The increase in voltage switches on transistors Q3 and Q4. As a result, transistor Q3 begins to conduct through resistor R4 and main switching transistor Q4 begins to conduct through the "load," thereby switching on the electrical circuit.

As a result of the current flowing through transistor Q3, the gate of transistor Q2 is connected to ground through transistor Q3, irrespective of whether or not transistor Q1 is conducting. At this stage, the transistors (Q2, Q3 & Q4) are latched to the conducting state, even if the piezoelectric voltage on transistor Q1 is subsequently reduced to zero and transistor Q1 ceases to conduct. Thus, main switching transistor Q4 will remain on until switch S1 is opened.

In order to deactivate or open the switch 400, switch S1 must be opened, for example, while there is no acoustic excitation of the piezoelectric transducer. If this occurs, the gate of transistor Q2 increases to +3V due to pull-up resistor R2. Transistor Q2 then switches off, thereby, in turn, switching off transistors Q3 and Q4. At this stage, the switch 400 returns to its sleep mode, even if switch S1 is again closed. The switch 400 will only return to its active mode upon receiving a new acoustic activation signal from the piezoelectric transducer.

It should be apparent to one of ordinary skill in the art that the above-mentioned electrical circuit is not the only possible implementation of a switch for use with the present invention. For example, the switching operation my be performed using a CMOS circuit, which may draw less current when switched on, an electromechanical switch, and the like.

Turning to FIGS. 3A–3G, a preferred embodiment of an acoustic transducer 1 is shown that includes a miniature flexural acoustic transducer capable of receiving external acoustic signals and producing an electrical output to "activate," i.e., deliver electrical current in or to an electrical circuit. Preferably, as explained above with respect to FIGS. 1A–1C, the electrical output from the acoustic transducer 118 is used to open and/or close the switch 120, allowing current flow in one or more the components of the electrical circuit 112, 212, 312. In addition, the electrical output from the acoustic transducer 118 may be transferred via a communications bus to other components of the implant 110, for example, to provide commands to a control circuit or internal processor.

In a preferred embodiment, the acoustic transducer 1 is configured for receiving relatively low frequency acoustic signals (up to several megahertz) for vibrating a piezoelectric layer 2 in the acoustic transducer 1 at its resonant frequency. Preferably, the acoustic transducer 1 may respond to acoustic excitation signal between about 20–60 kilohertz, and more preferably has a resonant frequency of about 40 kilohertz. Unlike high frequency waves (those greater than several megahertz), low frequency acoustic waves are generally only slightly attenuated by water-based tissues within the body. Consequently, low frequency acoustic waves may reach almost any point of the body, including deeply located organs, such as the heart, liver, or brain.

Returning to FIG. 3A, the transducer element 1 includes at least one cell member 3, including a cavity 4 etched into a substrate and covered by a substantially flexible piezoelectric layer 2. Preferably, the cavity 4 is etched into the substrate using conventional printed-circuit photolithography methods. Alternatively, the cavity 4 may be etched into the substrate using VLSI/micro-machining technology or any other suitable technology.

Figure 3A:
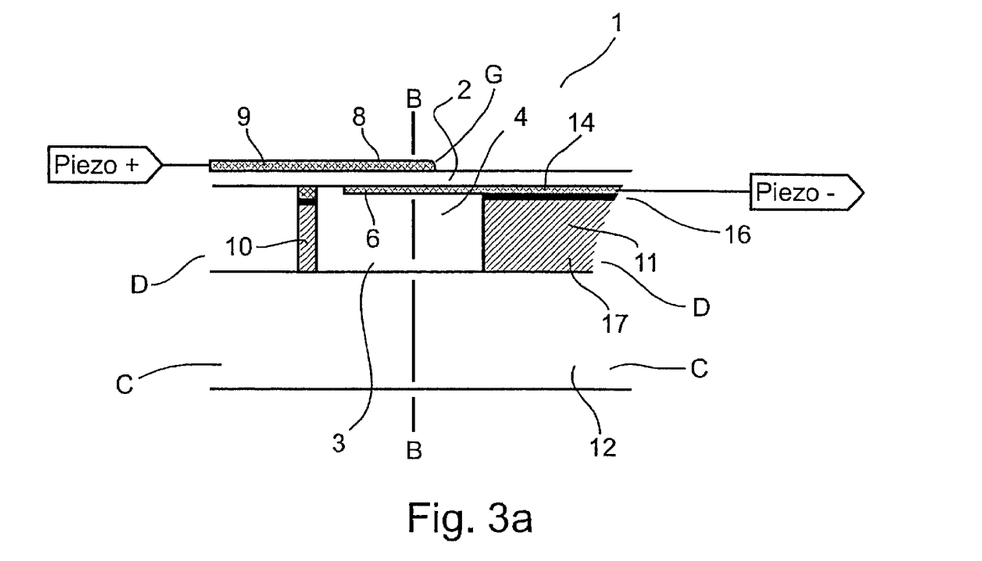
FIG. 3A is a cross-sectional view of an acoustic transducer element, in accordance with the present invention.

The cavity 4 preferably includes a gas, such as air, providing a predetermined pressure within the cavity 4 that may be selected to provide a desired sensitivity and ruggedness of the transducer, as well as to at least partially define the resonant frequency of the piezoelectric layer 2. An upper electrode 8 and a lower electrode 6 are attached to the piezoelectric layer 2, the electrodes 6, 8 being coupled to the switch 400, for example, at points Piezo+ and Piezo−, as described above with reference to FIG. 2. The substrate is preferably made of an electrical conducting layer 11 disposed on an electrically insulating layer 12, such that the cavity 4 is etched substantially through the thickness of electrically conducting layer 11.

The electrically conducting layer 11 is preferably made of copper and the insulating layer 12 is preferably made of a polymer such as polyamide. Conventional copper-plated polymer laminate such as Kapton™ sheets may be used for the production of the transducer element 1. Alternatively, commercially available laminates, such as Novaclad™, may be used. In a further alternative, the substrate may include a silicon layer, or any other suitable material, and/or the electrically conducting layer 11 may be made of a non-conductive material such as Pyralin™.

According to a preferred embodiment, the cavity 4 features a circular or hexagonal shape with radius of about 200 $\mu$m. The electrically conducting layer 11 preferably has a thickness of about 15 $\mu$m. The cell member 3 is preferably etched completely through the thickness of the electrically conducting layer 11. The electrically insulating layer 12 preferably features a thickness of about 50 $\mu$m. The piezoelectric layer 2 may be made of PVDF or a copolymer thereof. Alternatively, piezoelectric layer 2 may be made of a substantially flexible piezoceramic. In a preferred embodiment, the piezoelectric layer 2 is a poled PVDF sheet having a thickness of about 9–28 $\mu$m.

Figure 3B:
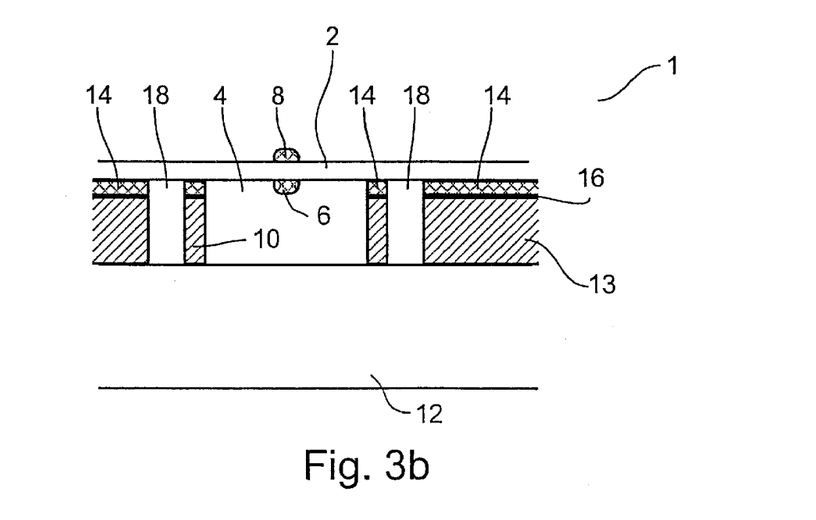
FIG. 3B is a cross-sectional view of the transducer element of FIG. 3A, taken along line B—B.
Figure 3C:
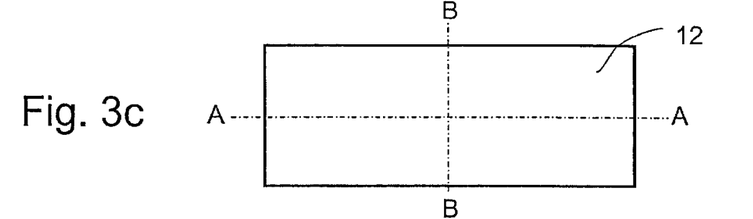
FIG. 3C is a cross sectional view of the transducer element of FIG. 3A, taken along line C—C.
Figure 3D:
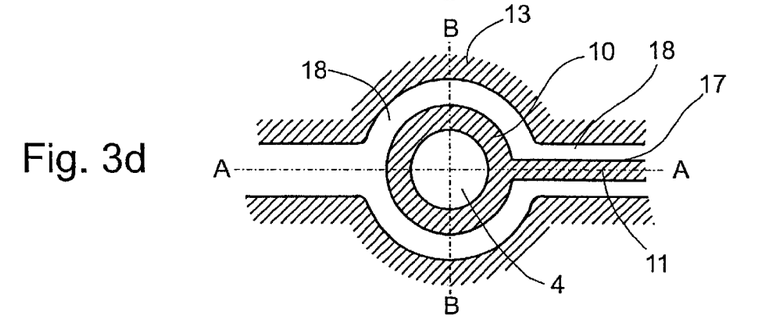
FIG. 3D is a cross sectional view of the transducer element of FIG. 3A, taken along line D—D.
Figure 3E:
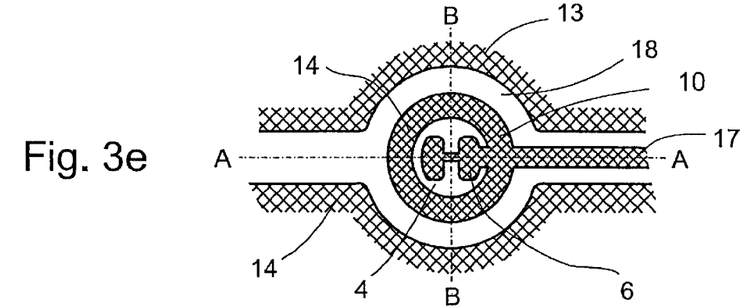
FIG. 3E is a cross sectional view of the transducer element of FIG. 3A, taken along line E—E.
Figure 3F:
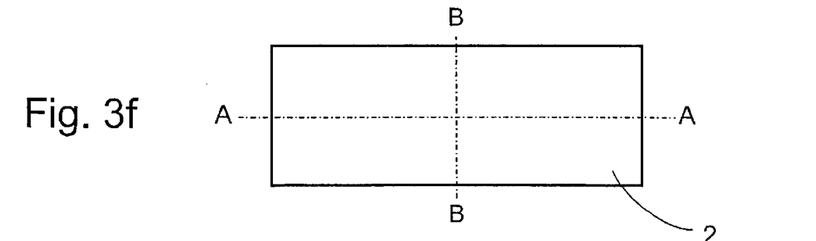
FIG. 3F is a cross sectional view of the transducer element of FIG. 3A, taken along line F—F.
Figure 3G:
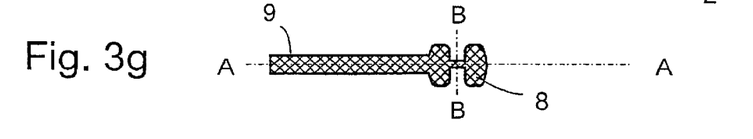
FIG. 3G is a cross sectional view of the transducer element of FIG. 3A, taken along line G—G.

As best seen in FIG. 3D, an insulating chamber 18 is etched into the substrate, preferably through the thickness of the conducting layer 11, so as to insulate the transducer element from other portions of the substrate that may include other electrical components, such as other transducer elements etched into the substrate. According to a specific embodiment, the width of the insulating chamber 18 is about 100 $\mu$m. As shown, the insulating chamber 18 is etched into the substrate so as to form a wall 10 of a predetermined thickness enclosing the cavity 4, and a conducting line 17 is integrally made with the wall 10 for connecting the transducer element to another electronic component preferably etched into the same substrate, or to an external electronic circuit (not shown). The upper electrode 8 and lower electrode 6 are preferably precisely shaped so as to cover a predetermined area of the piezoelectric layer 2. The electrodes 6, 8 may be deposited on the upper and lower surfaces of the piezoelectric membrane 2, respectively, by using various methods such as vacuum deposition, mask etching, painting, and the like.

As shown in FIG. 3B, the lower electrode 6 is preferably made as an integral part of a substantially thin electrically conducting layer 14 disposed on electrically conducting layer 11. Preferably, electrically conducting layer 14 is made of a Nickel-Copper alloy and is attached to the electrically conducting layer 11 by means of a sealing connection 16, which may be made of indium. According to a preferred embodiment, the sealing connection 16 may feature a thickness of about 10 μm, such that the overall height of wall 10 of cavity 4 is about 20–25 μm.

It will be appreciated that the precise dimensions of the various elements of a transducer element in accordance with the present invention may be specifically tailored according to the requirements of the specific application, and should not be limited to the exemplary dimensions provided herein. For example, the thickness and radius of the piezoelectric layer 2, as well as the pressure within cavity 4, may be specifically selected so as to provide a predetermined resonant frequency.

By using a substantially flexible piezoelectric layer 2, a miniature transducer element is provided that has a resonant frequency having an acoustic wavelength that is much larger than the extent of the transducer. This enables the transducer to be omnidirectional even at resonance, and further allows the use of relatively low frequency acoustic signals that do not suffer from significant attenuation in the surrounding medium. Thus, the transducer element may be suitable for application in confined or hidden locations where the orientation of the transducer element may not be ascertained in advance.

Returning to FIGS. 3A, 3B, and 3E, the electrically conducting layer 14 covers the various portions of the conducting layer 11, including wall 10 and conducting line 17. The portion of the conducting layer 14 covering the conducting line 17 may be used for connection to an electronic component, such as a neighboring cell.

Figure 4:
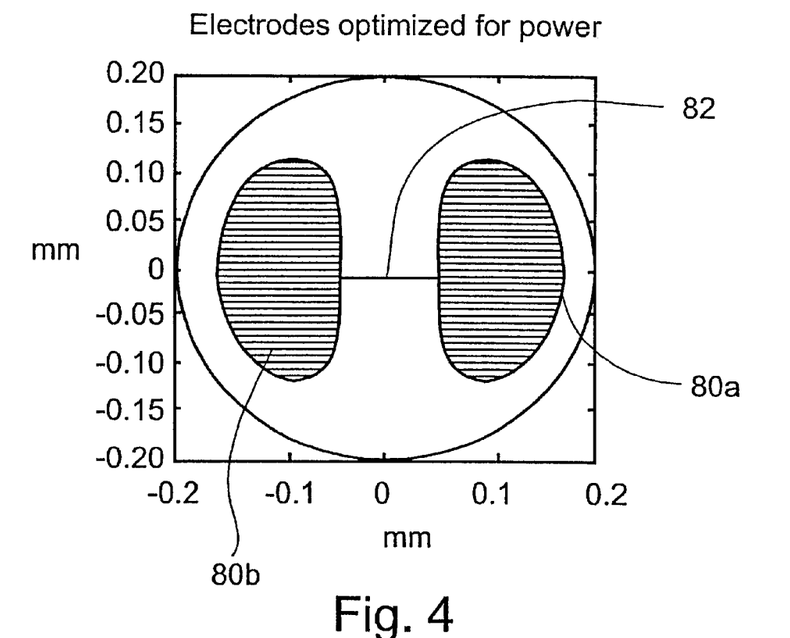
FIG. 4 is a top view of a preferred embodiment of an electrode shaped for maximizing the power response of a transducer, in accordance with the present invention.

According to a preferred embodiment, the electrodes 6, 8 are specifically shaped to include the most energy-productive region of the piezoelectric layer 2 so as to provide maximal response of the transducer while optimizing the electrode area, and therefore the cell capacitance, thereby maximizing a selected parameter such as voltage sensitivity, current sensitivity, or power sensitivity of the transducer element. Turning to FIG. 4, a preferred electrode shape for maximizing the power response of the transducer is shown in which the electrode includes two electrode portions 80a and 80b substantially covering the maximal charge density portions of layer 2, the electrode portions being interconnected by means of a connecting member 82 having a minimal area. Preferably, the electrode portions 80a and 80b cover the portions of piezoelectric layer 2 that yield at least a selected threshold (e.g. 30%) of the maximal charge density.

According to the present invention any other parameter may be optimized so as to determine the shape of electrodes 6 and 8. According to further features of the present invention, only one electrode (either the upper electrode 8 or lower electrode 6) may be shaped so as to provide maximal electrical response of the transducer, with the other electrode covering the entire area of the piezoelectric layer 2. Since the charge is collected only at the portions of the piezoelectric layer 2 received between the upper and lower electrodes 8, 6, this configuration may be operatively equivalent to a configuration including two shaped electrodes having identical shapes.

Figure 5:
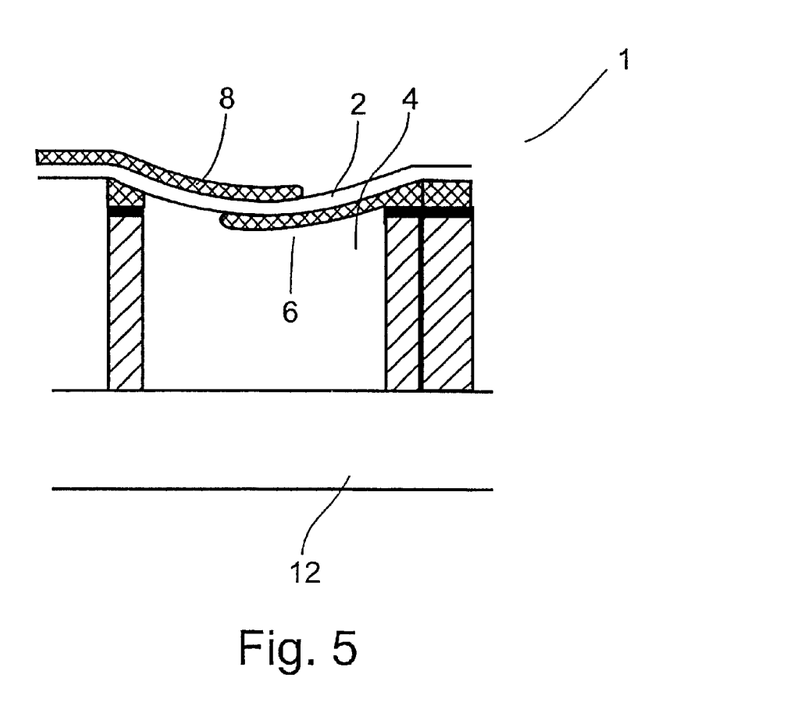
FIG. 5 is a cross-sectional view of another preferred embodiment of a transducer element, in accordance with the present invention.

Turning to FIG. 5, another preferred embodiment of a acoustic transducer is shown, including a transducer element 1 over a chamber 4 that may contain gas at a substantially low pressure, thereby conferring a substantially concave shape to the piezoelectric membrane 2 at equilibrium. This configuration may enhance the electrical response of the transducer by increasing the total charge obtained for a given displacement of layer 2. For example, this embodiment may increase the charge output of the piezoelectric layer 2 for a given displacement, thereby increasing the voltage, current and power responses of the transducer without having to increase the acoustic pressure. Further, it may further facilitate miniaturization of the transducer since the same electrical response may be obtained for smaller acoustic deflections. This transducer may also be substantially more robust mechanically and therefore more durable than the first embodiment described above with respect to FIGS. 3A–3G. This further miniaturization may also allow higher resonance frequencies relative to the embodiment shown of FIGS. 3A–3G.

An acoustic transducer element according to the present invention may also be used as a transmitter, for example, for transmitting information from an implant to a remote receiver, e.g., by modulating the reflection of an external impinging acoustic wave arrived from a remote transmitter. The transducer element generally functions as a transmitter element due to the asymmetric fluctuations of the piezoelectric layer with respect to positive and negative transient acoustic pressures obtained as a result of the pressure differential between the interior and exterior of the underlying cavity.

The transmitter element preferably modulates the reflection of an external impinging acoustic wave by means of a switching element connected thereto, e.g., in the electrical circuit of an implant as described above. The switching element may encode the information that is to be transmitted, such as the output of a sensor, thereby frequency modulating a reflected acoustic wave. This may require very little expenditure of energy from the transmitting module itself, since the acoustic wave that is received is externally generated, such that the only energy required for transmission is the energy of modulation. Specifically, the reflected acoustic signal is modulated by switching the switching element according to the frequency of a message electric signal arriving from another electronic component such as a sensor, so as to controllably change the mechanical impedance of the piezoelectric layer according to the frequency of the message signal. Preferably, the invention uses a specific array of electrodes connected to a single cell member or alternatively to a plurality of cell members so as to control the mechanical impedance of the piezoelectric layer.

Figure 6A:
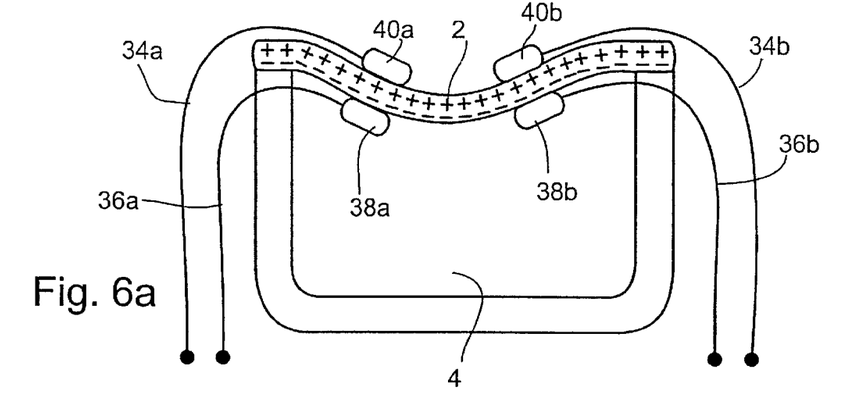
FIGS. 6A–6F are schematic views of exemplary embodiments of an acoustic transmitter that may be used as a transmitter, in accordance with the present invention.

FIGS. 6A–6F show exemplary configurations of a transducer element including a piezoelectric layer 2 that may be controllably changed to provide a transmitter. Referring to FIG. 6A, the transmitter element may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit (not shown) by means of conducting lines 36a, 36b, 34a and 34b, respectively, the electrical circuit including a switching element (also not shown) so as to alternately change the electrical connections of the conducting lines 36a, 36b, 34a and 34b.

Preferably, the switching element switches between a parallel connection and an anti-parallel connection of the electrodes. A parallel connection decreases the mechanical impedance of the piezoelectric layer 2, and an anti-parallel connection increases the mechanical impedance of the piezoelectric layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor.

Figure 6B:
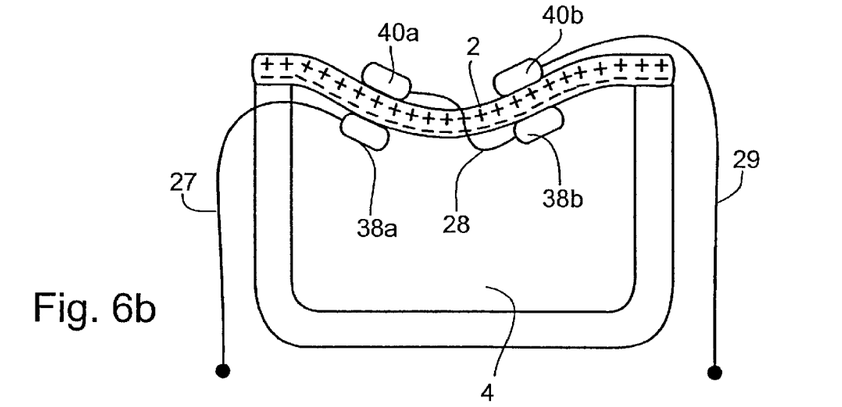

According to another embodiment, shown in FIG. 6B, upper electrode 40a is connected to lower electrode 38b by means of a conducting line 28, and electrodes 38a and 40b are connected to an electrical circuit by means of conducting lines 27 and 29, respectively, the electrical circuit including a switching element. This embodiment provides an anti-parallel connection of the electrodes such that the switching element functions as an on/off switch, thereby alternately increasing the mechanical impedance of the piezoelectric layer 2.

Figure 6C:
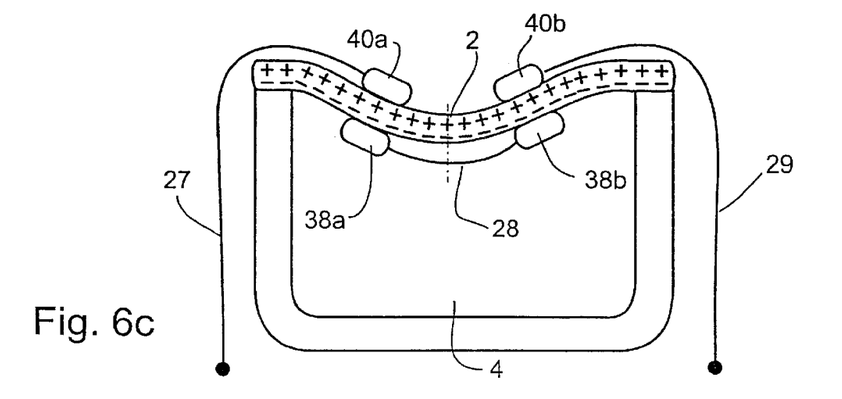

In order to reduce the complexity of the electrical connections, the piezoelectric layer 2 may be depolarized and then repolarized at specific regions thereof. As shown in FIG. 6C, the polarity of the portion of the piezoelectric layer 2 received between the electrodes 40a and 38a is opposite to the polarity of the portion of the piezoelectric layer 2 received between the electrodes 40b and 38b. An anti-parallel connection is thus achieved by interconnecting the electrodes 38a and 38b by means of a conducting line 28, and providing conducting lines 27 and 29 connected to the electrodes 40a and 40b, respectively, the conducting lines for connection to an electrical circuit including a switching element.

Figure 6D:
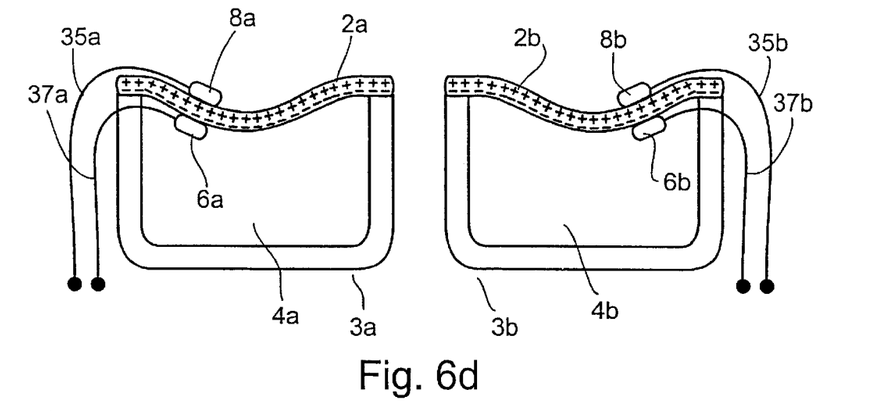

Turning to 6D, another embodiment is shown in which the transmitting element includes a plurality of transducing cell members, such that the mechanical impedance of piezoelectric layer 2 is controllably changed by appropriately interconnecting the cell members. A first transducing cell member 3a includes a layer 2a and a cavity 4a, and a second transducing cell member 3b includes a layer 2b and a cavity 4b that are preferably contained within the same substrate. A first pair of electrodes including electrodes 6a and 8a is attached to the piezoelectric layer 2, and a second pair of electrode including electrodes 6b and 8b is attached to the piezoelectric layer 2b. The electrodes 6a, 8a, 6b and 8b are electrically connected to an electrical circuit (not shown) by means of conducting lines 37a, 35a, 37b and 35b, respectively, the electrical circuit including a switching element so as to alternately switch the electrical connections of the conducting lines 37a, 35a, 37b and 35b so as to alternately provide parallel and anti-parallel connections, substantially as described for FIG. 6A, thereby alternately decreasing and increasing the mechanical impedance of the piezoelectric layers 2a and 2b.

Figure 6E:
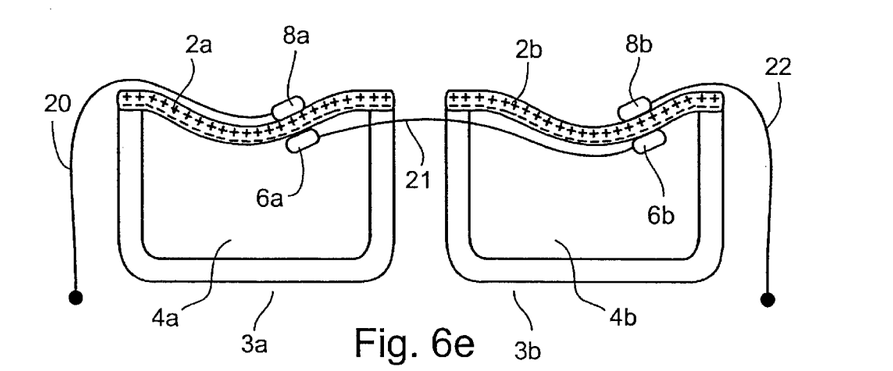

FIG. 8E shows another embodiment in which the first and second transducing cell members are interconnected by means of an anti-parallel connection. As shown, the polarity of piezoelectric layer 2a is opposite to the polarity of layer 2b so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit including a switching element (not shown), wherein the switching element preferably functions as an on/off switch that alternately increases the mechanical impedance of the piezoelectric layers 2a and 2b.

Figure 6F:
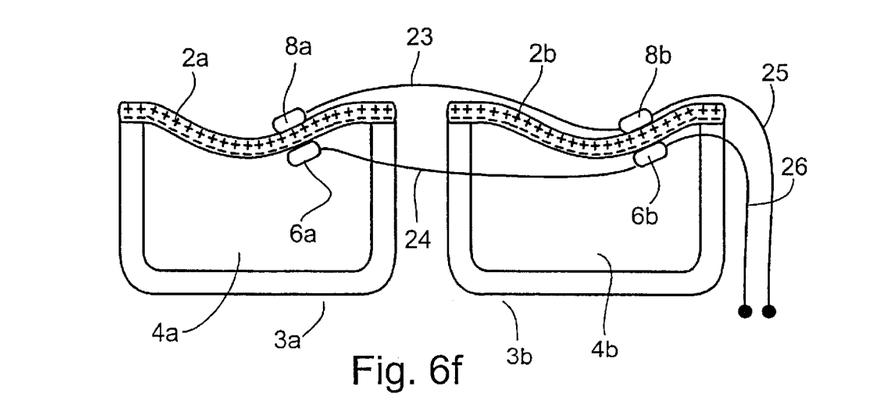

FIG. 68F shows another embodiment in which the first and second transducing cell members are interconnected by means of a parallel connection. As shown, electrodes 6a and 6b are interconnected by means of conducting line 24, electrodes 8a and 8b are interconnected by means of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 7:
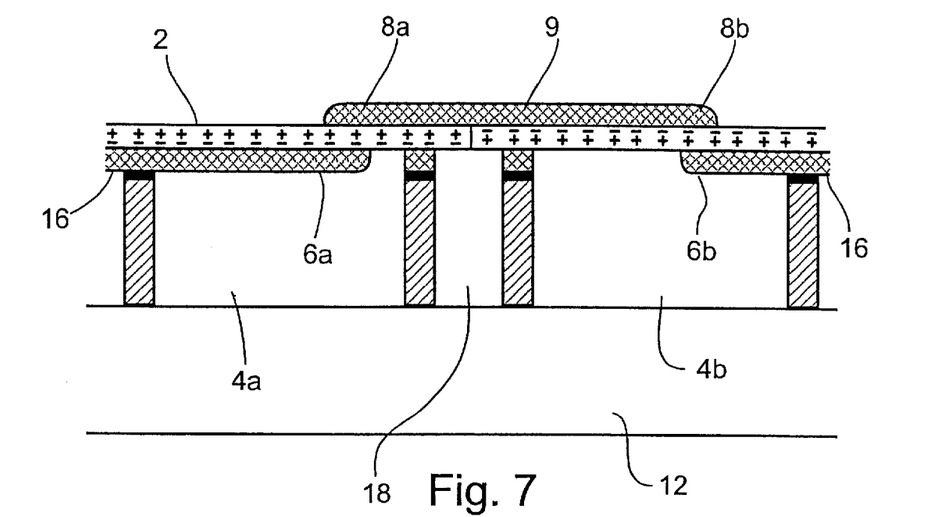
FIG. 7 is a cross-sectional view of another preferred embodiment of a transmitter element, in accordance with the present invention.

FIG. 7 shows a possible configuration of two transducing cell members etched onto the same substrate and interconnected by means of an anti-parallel connection. As shown, the transducing cell members are covered by a common piezoelectric layer 2, wherein the polarity of the portion of the piezoelectric layer 2 received between electrodes 6a and 8a is opposite to the polarity of the portion of the piezoelectric layer 2 received between electrodes 6b and 8b. The electrodes 8a and 8b are bonded by means of a conducting line 9, and the electrodes 6a and 6b are provided with conducting lines 16 for connection to an electrical circuit (not shown).

Figure 8:
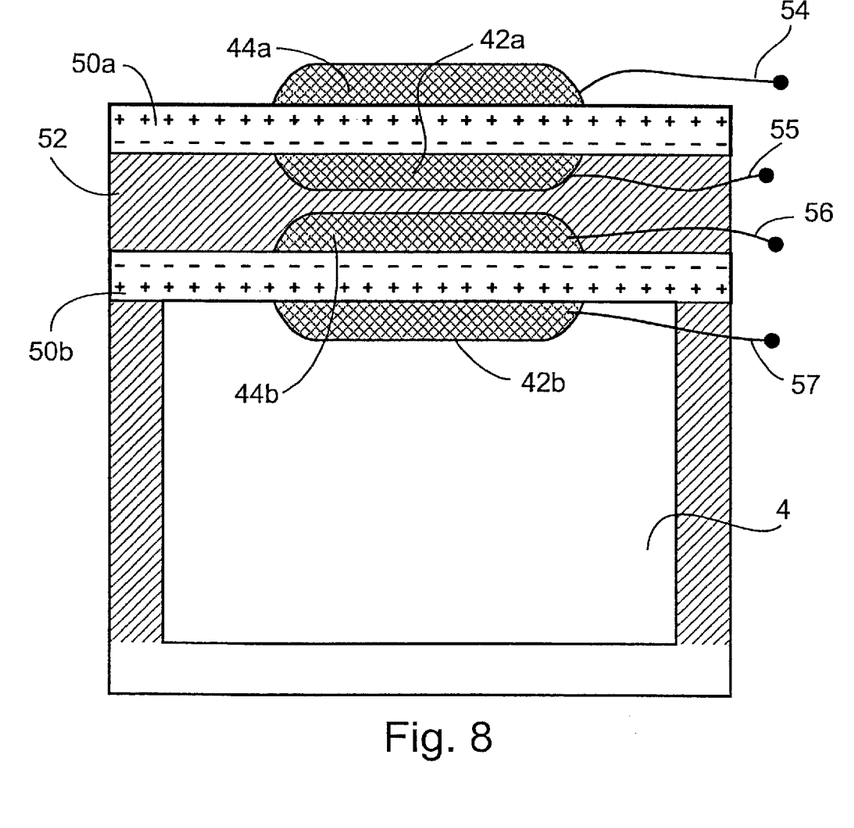
FIG. 8 is a cross-sectional view of still another preferred embodiment of a transmitter element, in accordance with the present invention.

Yet another embodiment of a transmitter element according to the present invention is shown in FIG. 8. The transmitter element includes a transducing cell member having a cavity 4 covered by a first and second piezoelectric layers 50a, 50b, preferably having opposite polarities. Preferably, the piezoelectric layers 50a, 50b are interconnected by means of an insulating layer 52. Upper and lower electrodes 44a, 42a are attached to the piezoelectric layer 50a, and upper and lower electrodes 44b and 42b are attached to the piezoelectric layer 50b. The electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of the present invention.

What is claimed is:

1. An implant for surgical insertion, implantation, or location within a body, comprising:
    an electrical circuit configured for performing one or more commands when the implant is activated;
    a sensor coupled to the electrical circuit for measuring a physiological parameter within the body, the one or more commands comprising activating the sensor to measure a physiological parameter within the body;
    an energy storage device;
    a switch coupled to the electrical circuit and the energy storage device; and
    an acoustic transducer coupled to the switch, the acoustic transducer being activatable upon acoustic excitation by an external acoustic energy source for closing the switch to allow current flow from the energy storage device to the electrical circuit, the acoustic transducer further configured for transmitting an acoustic signal proportional to the physiological parameter to a receiver external to the body.

2. The implant of claim 1, wherein the switch is configured such that the switch is closed only when the acoustic transducer receives a first acoustic excitation signal followed by a second acoustic excitation signal, the first and second acoustic excitation signals being separated by a predetermined delay.

3. The implant of claim 1, wherein the acoustic transducer is configured for receiving a first acoustic excitation signal and a second acoustic excitation signal, the switch being closed when the first acoustic excitation signal is received by the acoustic transducer, and the switch being opened when the second acoustic excitation signal is received by the acoustic transducer for discontinuing current flow from the energy storage device to the electrical circuit.

4. The implant of claim 1, further comprising a therapeutic device coupled to the electrical circuit, the electrical circuit being configured for controlling the therapeutic device in response to the physiological parameter measured by the sensor.

5. The implant of claim 1, wherein the one or more commands comprises activating an actuator coupled to the electrical circuit, the actuator being configured for controlling a therapeutic device coupled to the actuator.

6. The implant of claim 1, wherein the acoustic transducer comprises:
   a cell member having a cavity;
   a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
   a first electrode attached to the external surface and a second electrode attached to the internal surface.

7. The implant of claim 1, wherein the energy storage device comprises a battery.

8. The implant of claim 1, wherein the energy storage device comprises a rechargeable device, the rechargeable device being rechargeable by a device external to the body.

9. The implant of claim 1, wherein the acoustic transducer is configured for receiving a first acoustic excitation signal followed by a second acoustic excitation signal, the electrical circuit configured for interpreting the second acoustic excitation signal as one of a predetermined set of commands.

10. The implant of claim 1, further comprising a timer coupled to the switch, the timer configured for opening the switch after a predetermined time has passed after the switch is initially closed.

11. A method for transmitting information to an implant comprising an acoustic switch coupled to an electrical circuit and an energy storage device, the implant being located within a body, the method comprising:
   transmitting one or more acoustic signals comprising an acoustic activation signal and an acoustic command signal from a source located outside of the body towards the implant; and
   closing the acoustic switch in response to the acoustic activation signal, whereupon current flows from the energy storage device to the electrical circuit;
   wherein the acoustic switch sends an electrical command signal to the electrical circuit in response to the acoustic command signal.

12. The method of claim 11, wherein the electrical circuit performs one or more commands in response to the electrical command signal when the switch is closed.

13. The method of claim 12, wherein the one or more commands comprises measuring a physiological parameter within the body.

14. The method of claim 13, further comprising transmitting a signal proportional to the physiological parameter from the implant to a receiver located outside the body.

15. The method of claim 13, wherein the one or more commands comprises controlling a therapeutic device within the body in response to the physiological parameter.

16. The method of claim 11, wherein the acoustic switch remains closed until the energy storage device is depleted.

17. The method of claim 11, wherein the acoustic switch automatically opens after a predetermined time to discontinue current flow from the energy storage device to the electrical circuit.

18. The method of claim 11, further comprising transmitting an acoustic termination signal from a source located outside of the body towards the implant, the acoustic switch opening in response to the acoustic termination signal to discontinue current flow from the energy storage device to the electrical circuit.

19. The method of claim 11, wherein the acoustic activation signal comprises a first acoustic excitation signal and a second acoustic excitation signal separated by a predetermined delay.

20. The method of claim 11, wherein the electrical circuit interprets the electrical command signal to perform one or more pre-defined commands.

21. The method of claim 11, wherein the electrical circuit performs one of a plurality of known commands in response to the electrical command signal.

22. The method of claim 11, further comprising charging the energy storage device with an energy source located outside the body before transmitting the acoustic activation signal.

23. A method for exchanging information with an implant comprising an acoustic switch including an acoustic transducer, an electrical circuit coupled to the acoustic switch, and an energy storage device, the implant being located within a body, the method comprising:
   transmitting an acoustic activation signal to the acoustic transducer from a source located outside of the body towards the implant, the acoustic switch closing in response to the acoustic activation signal, whereupon current flows from the energy storage device to the electrical circuit;
   measuring a physiological parameter within the body with the implant; and
   receiving an acoustic signal proportional to the physiological parameter from the implant with a receiver located outside the body.

24. The method of claim 23, wherein the acoustic signal received from the implant is transmitted by the acoustic transducer.

25. The method of claim 23, wherein the acoustic signal received from the implant is transmitted by a separate transmitter than the acoustic transducer.

26. The method of claim 23, wherein the acoustic activation signal comprises a first acoustic excitation signal and a second acoustic excitation signal separated by a predetermined delay.

* * * * *